(12) United States Patent
Leitner

(10) Patent No.: US 7,331,932 B2
(45) Date of Patent: Feb. 19, 2008

(54) METHOD AND DEVICE FOR DETERMINING THE MECHANICAL AXIS OF A FEMUR

(75) Inventor: François Leitner, Uriage (FR)

(73) Assignee: Aesculap AG & Co. KG, Tuttlingen (DE)

( * ) Notice: Subject to any disclaimer, the term of this patent is extended or adjusted under 35 U.S.C. 154(b) by 777 days.

(21) Appl. No.: 10/460,637

(22) Filed: Jun. 11, 2003

(65) Prior Publication Data

US 2004/0034313 A1  Feb. 19, 2004

Related U.S. Application Data

(63) Continuation of application No. PCT/EP01/12141, filed on Oct. 20, 2001.

(30) Foreign Application Priority Data

Dec. 15, 2000 (DE) ............... 100 62 580

(51) Int. Cl.
*A61B 5/103* (2006.01)
*A61B 5/117* (2006.01)

(52) U.S. Cl. .............. 600/595; 600/587; 600/592; 600/594

(58) Field of Classification Search .......... 600/595, 600/587, 592, 594

See application file for complete search history.

(56) References Cited

U.S. PATENT DOCUMENTS 5,249,581 A   10/1993  Horbal et al.
5,482,055 A * 1/1996  Smith ............... 600/595
5,611,353 A   3/1997  Dance et al.
6,385,475 B1  5/2002  Cinquin et al.

FOREIGN PATENT DOCUMENTS

| WO | 95/00075 | 1/1995 |
| WO | 98/40037 | 9/1998 |
| WO | 00/48507 | 8/2000 |

* cited by examiner

*Primary Examiner*—Max Hindenburg
*Assistant Examiner*—Jeffrey G Hoekstra
(74) *Attorney, Agent, or Firm*—Lipsitz & McAllister, LLC

(57) ABSTRACT

In order to avoid the use of a marking element on the pelvic bone in a method for determining the mechanical axis of a femur, with which the femur is moved about the hip joint, the movement of the femur is followed via a navigation system by means of a marking element on the femur, position data of the femur obtained therefrom are stored and the position of the mechanical axis of the femur is calculated relative to the same from the various position data of the femur in various positions, it is suggested that the femur be pivoted from an initial position only through a maximum pivoting angle of 15° in various directions and that the mechanical axis of the femur be calculated from the position data of the surface area thereby covered by the marking element and from the position data of the knee joint otherwise determined. In addition, a device for carrying out this method is described.

21 Claims, 3 Drawing Sheets

METHOD AND DEVICE FOR DETERMINING THE MECHANICAL AXIS OF A FEMUR

The present disclosure relates to the subject matter disclosed in International application No. PCT/EP01/12141 of Oct. 20, 2001, which is incorporated herein by reference in its entirety and for all purposes.

BACKGROUND OF THE INVENTION

The invention relates to a method for determining the mechanical axis of a femur, with which the femur is moved about the hip joint, the movement of the femur is followed via a navigation system by means of a marking element on the femur, position data of the femur obtained therefrom are stored and the position of the mechanical axis of the femur is calculated relative to the same from the various position data of the femur in various positions.

WO 98/40037 describes such a method, wherein marking elements are attached to the hip and to the femur for determining the mechanical axis of the femur, the movement of these marking elements during pivoting of the femur about the hip joint being recorded; the position of the hip joint is determined from the position data of the marking element on the hip, on the one hand, and on the femur, on the other hand, and the mechanical axis of the femur may then be determined from the position of the hip joint and the position of the knee joint determined in a different way.

This method operates reliably but has the disadvantage that an additional marking element must be arranged on the hip bone and this is complicated and, in certain circumstances, entails additional pain for the patient.

The object of the invention is to develop a generic method such that a faultless determination of the position of the mechanical axis of the femur is also possible when a marking element is arranged only on the femur.

SUMMARY OF THE INVENTION

This object is accomplished in accordance with the invention, in a method of the type described at the outset, in that the femur is pivoted from an initial position only through a maximum pivoting angle of 15° in various directions and that the mechanical axis of the femur is calculated from the position data of the surface area covered by the marking element and from the position data of the knee joint otherwise determined.

With this method, the femur is pivoted relative to the pelvic bone, in which the femur is rotatably mounted, only through a very small pivoting angle which is at the most 15°, preferably less than this, for example, at the most 10° or even less. With such small pivoting angles, it may be assumed that the pelvis will not be moved appreciably during this pivoting movement and retains its position without any additional fixing which may be painful. As a result, with this very small pivoting movement of the femur this is pivoted about a hip joint which is arranged more or less stationary in the space and this leads to the marking element moving during this pivoting movement on a partial spherical surface, the center point of which is essentially determined by the hip joint. The position of the mechanical axis of the femur may then be calculated from the position data of this partial spherical surface, which is passed over, without any monitoring of the position of the pelvis being necessary for this purpose. With this method it is, therefore, sufficient to follow the movement of the femur and, therefore, it is also sufficient when a marking element is secured only on the femur.

In a preferred embodiment it is provided for only position data to be used for the calculation of the mechanical axis which correspond to a pivoting angle which is less than a predetermined critical angle which is smaller than the maximum pivoting angle covered by the femur. This critical angle can, in particular, be between 4° and 6°.

As a result of the restriction to those position data which are obtained during a particularly small pivoting movement, care is taken to an increased degree that the pelvis is not moved during the pivoting movement, i.e., the hip joint remains stationary. Any pivoting in this order of magnitude leads to a relatively small pivoting surface area of the marking element; this can, for example, be located within a circle having a radius of 8 cm.

On the other hand, it may also be provided for only position data to be used for the calculation of the mechanical axis which correspond to a pivoting angle which is more than a predetermined minimum angle which is smaller than the critical angle. For example, the minimum angle can be more than 3°.

With such a method, only position data are used which are located between the minimum angle and the critical angle during any deflection of the femur out of the initial position, i.e., only in a narrow circular ring area and, as a result, the accuracy, with which the position data of the surface covered by the marking element are determined, may be increased.

It may be provided, in particular, for all the stored position data to be left out of consideration when the actual pivoting angle of the femur relative to its initial position exceeds the maximum pivoting angle. In other words, such a measurement is invalid when a maximum pivoting angle is exceeded, for example, a maximum pivoting angle of 15° since there is then the risk of the pelvis and, therefore, the hip joint being moved due to the relatively large pivoting angle. Only when such a maximum pivoting angle is not exceeded during the pivoting movement will the position data stored during the measurement be taken into consideration for the subsequent calculation of the mechanical axis of the femur. If the maximum pivoting angle is exceeded once, the entire measurement has to be repeated.

In order to be able to determine the position of the mechanical axis of the femur from the stored position data, it is preferably provided for the center point of the partial spherical surface covered by the marking element to be calculated for the calculation of the mechanical axis of the femur from this partial spherical surface and for the mechanical axis to be determined by means of the connecting line of this center point to the knee joint.

Since the partial spherical surface is very small, the accuracy, with which the exact position of the center point of the partial spherical surface can be determined, is possibly somewhat restricted, in particular, with respect to the distance of this center point from the partial spherical surface.

In order to be able to bring about an improvement in this case, it may be provided in an additional, preferred embodiment of the invention for a virtual center point of the spherical surface to be determined first of all in that a plane is approximately calculated from the stored position data of the partial spherical surface and thereupon a vertical line extending through the knee joint and the virtual center is assumed to be at a predetermined distance from this plane on the vertical line and for the mechanical axis of the femur to then be calculated using the position data of the virtual center point and the position data of the partial spherical surface. The predetermined distance depends, of course, on the positioning of the marking element on the femur; this predetermined distance corresponds approximately to the distance of the marking element from the hip joint which can be estimated and, can, for example, be 40 cm; this parameter influences the accuracy of the method of calculation only relatively slightly.

It is, in addition, advantageous when the position data of the partial spherical surface are converted to a uniform pivoting angle relative to the initial position using the position data of the virtual center point so that corrected position data defining a common circle are obtained therefrom and when the mid-vertical of this circle is calculated as mechanical axis of the femur. All the position data obtained are, therefore, converted using the position data of the virtual center point, i.e., pivoted virtually about the virtual center point, such that the position data correspond to a pivoting angle which passes through the common circle. It has been shown that with this method of calculation the mechanical axis of the femur can be determined with great accuracy even proceeding from a relatively small partial spherical surface.

In an additional, preferred embodiment of the invention, it is provided for the number and the distribution of the measured position data to be determined in the entire pivoting area and for the recording of additional position data to be interrupted once a predetermined number and distribution are reached. As a result, it is ensured that the measurement is continued in any case for such a time until a sufficient number of measured position data are available in the entire pivoting area in order to be able to determine the spatial arrangement of the partial spherical surface covered by the marking element with sufficient accuracy.

It is also favorable when the stored position data are represented graphically in accordance with their spatial distribution in the pivoting area so that it is apparent what number of position data has been stored for which part of the possible pivoting area. The operator can immediately recognize from this graphic representation, in which area of the pivoting area additional position data still need to be determined, i.e., he can pivot the femur into this pivoting area which has not yet been measured adequately.

It may, in particular, be provided for sections of a surface area represented graphically to be marked in this surface area when a predetermined number of position data has been recorded in a part of the pivoting area of the femur corresponding to this section. This surface area can, in particular, be an annular surface area subdivided into segments. The operator can, therefore, recognize immediately from this representation whether enough position data are present in a certain area or not; for example, this can be brought about by a change in the color of a section of the surface area.

The invention also relates to a device for carrying out this method, comprising a navigation system for determining position data of a marking element secured on the femur and comprising a data processing unit for calculating the position of the mechanical axis of the femur from these position data.

Accordingly, the object underlying the invention is also to design a generic device such that an exact determination of the mechanical axis of the femur is possible with it without using a second marking element in the pelvic region and without the pelvis of the patient needing to be specially secured for this purpose.

This object is accomplished in accordance with the invention, in a device of the type described at the outset, in that for the calculation of the position of the mechanical axis of the femur the data processing unit selects from the position data those which correspond to a pivoting angle which is less than a predetermined critical angle which is smaller than the maximum pivoting angle covered by the femur. This limitation to position data which have been obtained during movement through small pivoting angles ensures that the pelvis and, with it, the hip joint have remained stationary during these small pivoting movements and so for the movement of the marking element a movement on a partial spherical surface results, the position data of which can be determined by means of the pivoting movement and used for the further calculation.

Additional, advantageous developments of such a device result from the patent claims.

The following description of a preferred embodiment of the invention serves to explain the invention in greater detail in conjunction with the drawings.

DETAILED DESCRIPTION OF THE INVENTION

Figure 1:
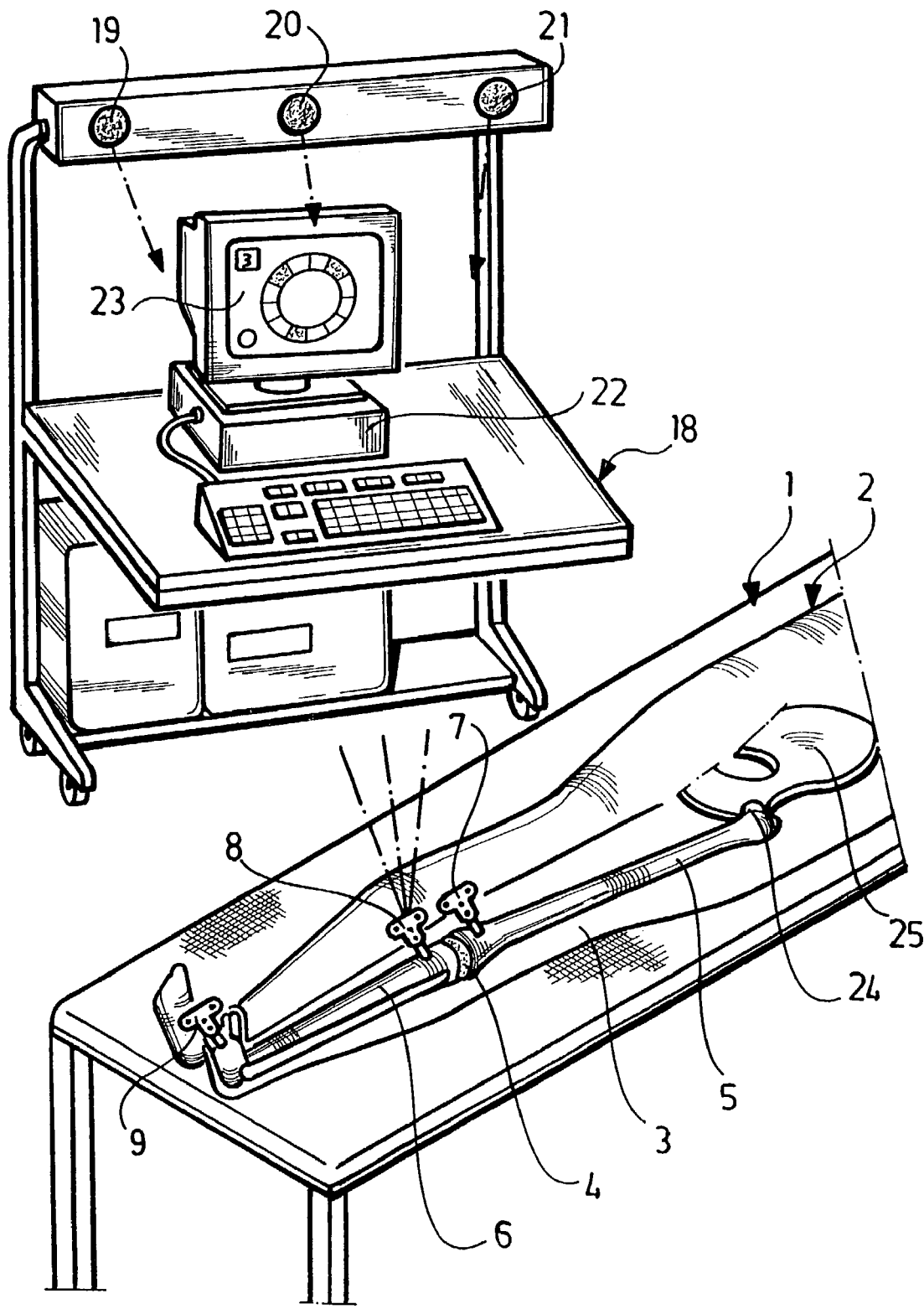
FIG. 1: shows a schematic view of a device for determining the mechanical axis of a femur.

A patient 2 lying on an operating table 1, for whom the knee joint 4 in one leg 3 is intended to be replaced by an endoprosthesis, is illustrated schematically in FIG. 1.

In order to prepare for this operation it is necessary to determine the orientation of the prosthesis parts to be used relative to the bones, i.e., relative to the femur or thigh bone 5 and, where applicable, also relative to the shin bone 6.

For this purpose, a marking element 7 is inserted into the femur 5 in the vicinity of the knee joint 4, for example, by screwing it in and, in addition, corresponding marking elements 8, 9 into the shin bone 6 which are not, however, of significance for the method of interest in this case.

Figure 2:
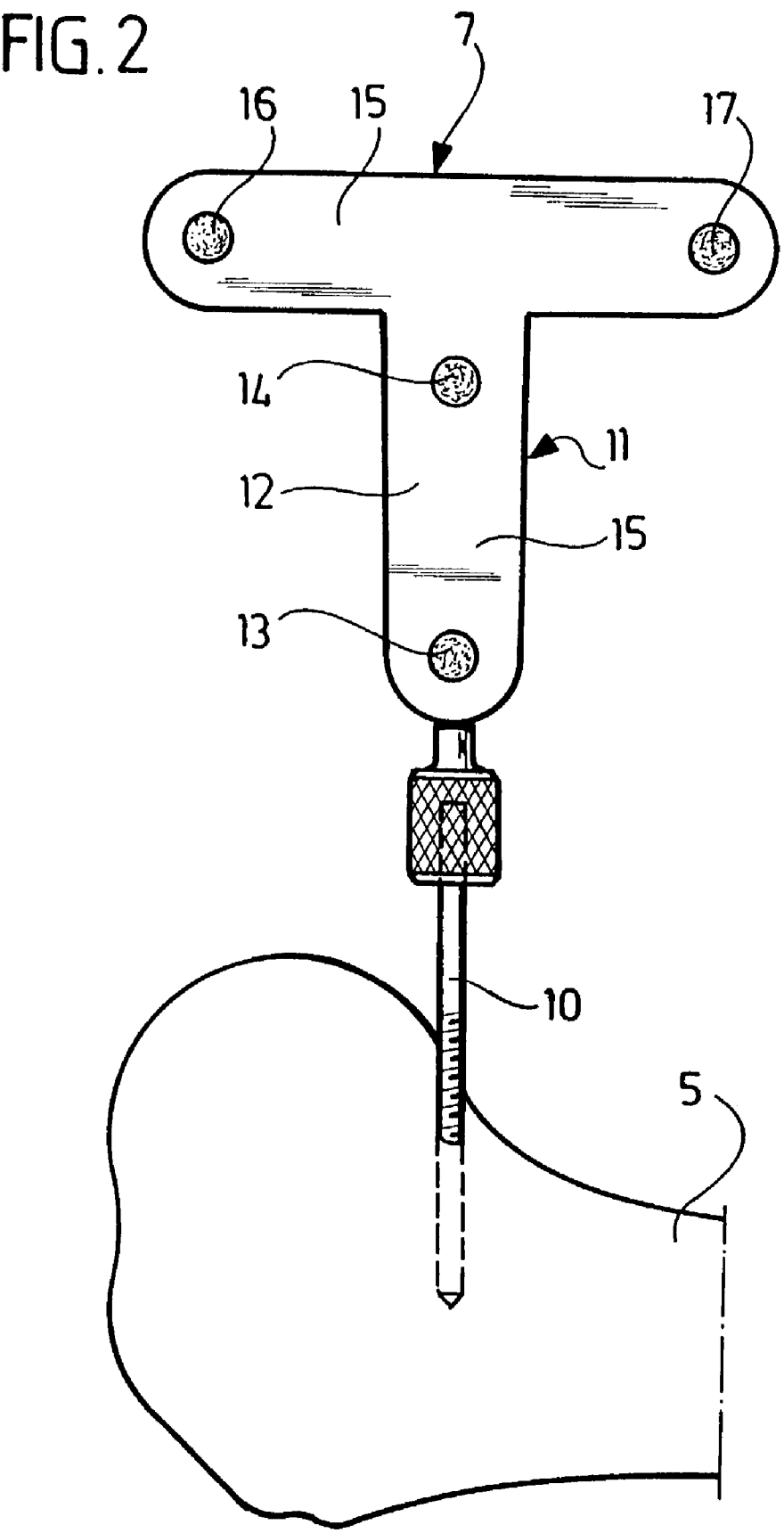
FIG. 2: shows a marking element inserted into the femur.

In FIG. 2, a marking element 7 of this type is illustrated; it comprises a foot 10 in the form of a bone screw which can be screwed into the femur and a T-shaped attachment member 11 which has two radiation transmitters 13, 14 at a distance from one another on its arm 12 extending parallel to the foot 10 and likewise two radiation transmitters 16, 17 on its transverse arm 15 adjoining the arm 12. These radiation transmitters may, for example, be ultrared diodes or ultrasonic transmitters. The attachment member 11 can be placed releasably on the foot 10 but only in a quite specific position so that even after the removal and after the re-attachment of such an attachment member 11 the radiation transmitters 13, 14, 16, 17 take up exactly the same position relative to the bone as that prior to the removal.

Three receiving devices 19, 20, 21 are arranged on a console 18 at a distance from one another and these receive the radiation which is transmitted by the radiation transmitters 13, 14, 16, 17. During the reception of radiation the receiving devices generate electrical signals which are fed to a data processing unit 22. On account of the different orientation of marking elements and receiving devices, differences in travel time result between transmission and reception of the radiation, and the data processing unit 22 can, in the case of the marking element 7, determine its position in the space completely on account of these differences in travel time and store these position data. It is, as a result, possible to generate in the data processing unit 22 sets of data which correspond to the position of the marking element 7 and, therefore, the femur 5 securely connected to it at specific times.

The receiving devices 19, 20, 21 may be designed in different ways; they may, as described, ascertain the orientation of the marking element as a result of differences in travel time; in principle, the determination of the orientation would also be possible as a result of a geometric measurement of the beam direction of beams which are transmitted by the radiation transmitters 13, 14, 16, 17.

In other developments, marking elements can also be used which have no radiation transmitters but rather reflection surface areas, at which radiation transmitted by the receiving device is reflected. These reflection surface areas may have, for example, a spherical shape.

It is merely essential for it to be possible, on account of the use of several receiving devices and several transmitters or reflection surface areas on the marking element, to determine the position of the marking element in the space definitively. Such an arrangement is designated in general as a navigation system.

The data processing unit 22 is provided with a screen 23, on which information for the user is shown as a function of recorded position data.

In order to determine the mechanical axis of the femur 5, the femur 5 is pivoted from any optional initial position about a point of rotation which is formed by the hip joint 24 which mounts the femur 5 on the pelvic bone 25 so as to be pivotable. With the method described here, the operator pivots the femur 5 proceeding from this initial position in all directions through a relatively small pivoting angle which is, for example, in the order of magnitude of 5° or a little more but does not, in any case, exceed a maximum pivoting angle which can, for example, be at 15°. Only a very small pivoting movement is therefore carried out and this leads to the pelvic bone 25 of the patient remaining stationary during this slight pivoting movement without special fixing measures needing to be taken for this purpose.

During the pivoting of the femur 5 in the pivoting area described, the marking element 7 moves on a partial spherical surface, the center point of which is arranged in the hip joint 24. The respective position of the marking element 7 is determined by the navigation system during the entire pivoting movement and corresponding sets of data are stored in the data processing unit 22. These sets of data indicate the position of the making element 7 at various times during the pivoting movement. Since the operator pivots the femur during the pivoting movement proceeding from the initial position in all directions, the positions of the marking element during the duration of the pivoting movement are therefore distributed over the entire partial spherical surface which limits a pivoting cone with a cone angle of at the most 15° at the base. The tip of this pivoting cone is located in the hip joint 24.

Figure 4A:
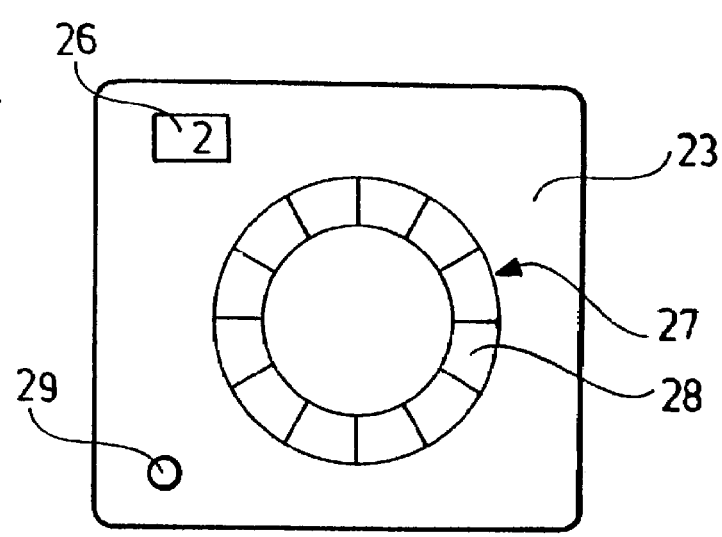
FIG. 4a: shows a schematic illustration of a screen for monitoring the recording of position data of the marking element during the pivoting movement of a femur prior to beginning this recording
Figure 4B:
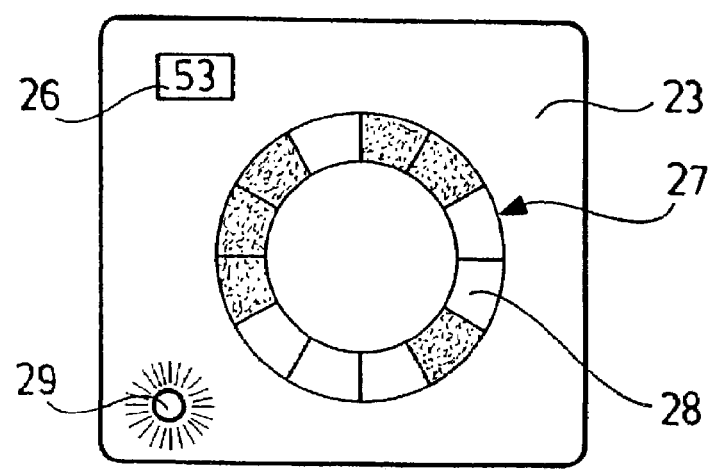
FIG. 4b: shows a view similar to FIG. 4a after finishing the recording.

The number of position data determined during this pivoting movement is indicated in a special window 26 on the screen 23; a circular ring 27 which is subdivided into a number of individual segments 28 is also represented on this screen. During the recording of the position data, not only are the recorded position data counted as a whole but it is also determined for each section of the pivoting area how many position data have been determined in this section. Each of these sections is associated with an individual segment of the illustrated circular ring 27 and as soon as sufficient position data have been collected in a specific section, the corresponding individual segment 28 is marked, for example, by a change in color. In the illustration of FIG. 4b, individual segments 28, which are associated with sections, in which enough position data have already been collected, are marked in a dark color; in the light-colored individual segments 28, on the other hand, the number of recorded position data has not yet reached a specific parameter. The operator can easily read from this, in what direction additional pivoting movements are still required in order to carry out the necessary number of measurements in this area, as well.

The data processing unit 22 monitors the fact that the pivoting angle is not increased beyond a maximum pivoting angle, for example, this maximum pivoting angle can be at 15°. When the operator exceeds this pivoting angle a signal is automatically indicated, for example, a luminous signal 29 on the screen and all the position data determined up to this point are rejected. The measurement process must then be repeated since it cannot be excluded that the pelvic bone 25 has been moved when the maximum pivoting angle is exceeded and so the hip joint 24 has not remained stationary.

When a measurement procedure has been ended in this manner without any interruption, i.e., without the maximum pivoting angle being exceeded, a set of data with a larger number of position data of the marking element 7 is available. The data processing unit 22 selects from these sets of data those, in which the pivoting angle is more than a minimum pivoting angle, for example, in the order of magnitude of 3° and less than a maximum critical angle, for example, in the order of magnitude of 6°. Only position data are therefore taken into consideration for further processing which correspond to pivoting angles between the minimum pivoting angle and the critical angle which, in the example illustrated, are between 3° and 6°.

In principle, it would be possible to calculate the center point of a partial spherical surface directly from the sets of position data which describe the partial spherical surface; this center point then indicates the position of the hip joint 24. If the position of this center point is connected to the position of the knee joint 4, which can be ascertained in a different way, for example, by scanning, this connecting line results in the mechanical axis of the femur which can be used for the orientation of surgical tools.

It is possible, in principle, to proceed in this way; since the partial spherical surface which the marking element 7 passes over is, however, very small, limitations with regard to accuracy can result during this direct determination of the center point of the partial spherical surface.

An improvement may be achieved when a plane is calculated first of all from the position data by means of a mathematical approximation method, this plane passing approximately through the positions of the marking element 7 during the pivoting process, and when a line is calculated therefrom which is at right angles to this plane and passes through the knee joint. According to the respective arrangement of the marking element 7 on the femur 5, a virtual center point can then be determined which is located on this line and is at a distance from the calculated plane which corresponds approximately to the actual distance of the marking element 7 from the hip joint 24; this last-named parameter is not very critical and can be included relatively roughly in the determination of the virtual center point.

Figure 3:
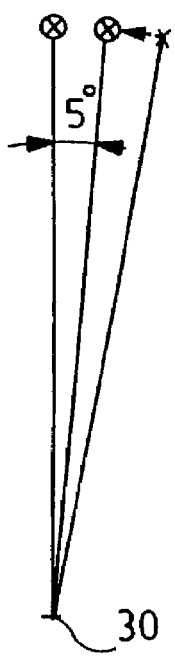
FIG. 3: shows a schematic illustration of the pivoting movement carried out by the femur and, therefore, by the marking element.

This virtual center point will be located in the vicinity of the actual hip joint 24 and used for a next calculation step. During this calculation step, all the position data which are associated with different pivoting angles are converted into position data which all have the same pivoting angle. In other words, the position data originally localized are pivoted about the virtual center point until the pivoting angle is the same for all the position data, i.e., all the position data are pivoted on a common circle, for example, with an opening angle of 5°. This is indicated in FIG. 3; here a set of position data for a pivoting angle which is greater than 5° is mathematically pivoted about the virtual center point 30 until it has reached a pivoting angle of 5°. In this way, all the measured position data can be used for determining a circle and the mechanical axis of the femur may be determined very easily from the geometric data of this circle in that the center axis of this circle is determined.

As a result of the method described, the accuracy of the determination of the position for the mechanical axis of the femur may be improved; as a result it is possible to calculate the position of the mechanical axis of the femur with the necessary precision even with a very small partial spherical surface, i.e., with very small pivoting angles.

The invention claimed is:

1. Method for determining the mechanical axis of a femur attached to a pelvis via a hip joint, comprising the steps of:
   moving the femur about the hip joint,
   following the movement of the femur via a navigation system by means of a marking element on the femur that passes over a surface area during said movement,
   storing position data of the femur obtained from the navigation system, and
   calculating the position of the mechanical axis of the femur from the stored position data of the femur in various positions,
   wherein:
   the femur is pivoted from an initial position only through a maximum pivoting angle of 15° in various directions to prevent movement of said pelvis,
   the mechanical axis of the femur is calculated from the position data of the surface area passed over by the marking element when the femur is moved and from position data of the knee joint;
   only position data corresponding to a pivoting angle less than a predetermined critical angle smaller than the maximum pivoting angle covered by the femur are used for the calculation of the mechanical axis; and
   the critical angle is between 4° and 6°.

2. Method as defined in claim 1, wherein the femur is pivoted only within a maximum pivoting angle of at most 10°.

3. Method as defined in claim 1, wherein only position data corresponding to a pivoting angle more than a predetermined minimum angle smaller than the critical angle are used for the calculation of the mechanical axis.

4. Method as defined in claim 1, wherein all the stored position data are left out of consideration when the actual pivoting angle of the femur relative to its initial position exceeds the maximum pivoting angle.

5. Method as defined in claim 1, wherein:
   the surface area passed over by the marking element when the femur is moved is a partial spherical surface, and
   for the calculation of the mechanical axis of the femur from the partial spherical surface a center point of this partial spherical surface is calculated and the mechanical axis is determined by means of a connecting line from this center point to the knee joint.

6. Method as defined in claim 5, comprising:
   determining a virtual center point of the partial spherical surface by calculating a plane from the stored position data of the partial spherical surface;
   assuming that a vertical line extending through the knee joint and the virtual center point is at a predetermined distance from the calculated plane on the vertical line; and
   calculating the mechanical axis of the femur using the position data of the virtual center point and the position data of the partial spherical surface.

7. Method as defined in claim 6, wherein the position data of the partial spherical surface are converted to a uniform pivoting angle relative to the initial position using the position data of the virtual center point so that corrected position data defining a common circle are obtained therefrom and wherein a mid-vertical of this circle is calculated as mechanical axis of the femur.

8. Method as defined in claim 1, wherein a number and distribution of the measured position data are determined in the entire pivoting area and the recording of additional position data is interrupted once a predetermined number and distribution are reached.

9. Method as defined in claim 1, wherein the stored position data are represented graphically in accordance with their spatial distribution in a pivoting area so that it is apparent what number of position data has been stored for which part of a possible pivoting area.

10. Method as defined in claim 9, wherein sections of a graphically represented surface area are marked when a predetermined number of position data is recorded in a corresponding part of the pivoting area of the femur.

11. Method as defined in claim 10, wherein the surface area is an annular surface area subdivided into segments.

12. Method for determining the mechanical axis of a femur attached to a pelvis via a hip joint, comprising the steps of:
   moving the femur about the hip joint,
   following the movement of the femur via a navigation system by means of a marking element on the femur that passes over a surface area during said movement,
   storing position data of the femur obtained from the navigation system, and
   calculating the position of the mechanical axis of the femur from the stored position data of the femur in various positions,
   wherein:
   the femur is pivoted from an initial position only through a maximum pivoting angle of 15° in various directions to prevent movement of said pelvis,
   the mechanical axis of the femur is calculated from the position data of the surface area passed over by the marking element when the femur is moved and from position data of the knee joint;
   only position data corresponding to a pivoting angle less than a predetermined critical angle smaller than the maximum pivoting angle covered by the femur are used for the calculation of the mechanical axis;
   only position data corresponding to a pivoting angle more than a predetermined minimum angle smaller than the critical angle are used for the calculation of the mechanical axis; and
   the minimum angle is more than 3°.

13. Method as defined in claim 12, wherein the femur is pivoted only within a maximum pivoting angle of at most 10°.

14. Method as defined in claim 12, wherein all the stored position data are left out of consideration when the actual pivoting angle of the femur relative to its initial position exceeds the maximum pivoting angle.

15. Method as defined in claim 12, wherein:
the surface area passed over by the marking element when the femur is moved is a partial spherical surface, and
for the calculation of the mechanical axis of the femur from the partial spherical surface a center point of this partial spherical surface is calculated and the mechanical axis is determined by means of a connecting line from this center point to the knee joint.

16. Method as defined in claim 15, comprising:
determining a virtual center point of the partial spherical by calculating a plane from the stored position data of the partial spherical surface;
assuming that a vertical line extending through the knee joint and the virtual center point is at a predetermined distance from the calculated plane on the vertical line; and
calculating the mechanical axis of the femur using the position data of the virtual center point and the position data of the partial spherical surface.

17. Method as defined in claim 16, wherein the position data of the partial spherical surface are converted to a uniform pivoting angle relative to the initial position using the position data of the virtual center point so that corrected position data defining a common circle are obtained therefrom and wherein a mid-vertical of this circle is calculated as mechanical axis of the femur.

18. Method as defined in claim 12, wherein a number and distribution of the measured position data are determined in the entire pivoting area and the recording of additional position data is interrupted once a predetermined number and distribution are reached.

19. Method as defined in claim 12, wherein the stored position data are represented graphically in accordance with their spatial distribution in a pivoting area so that it is apparent what number of position data has been stored for which part of a possible pivoting area.

20. Method as defined in claim 18, wherein sections of a graphically represented surface area are marked when a predetermined number of position data is recorded in a corresponding part of the pivoting area of the femur.

21. Method as defined in claim 19, wherein the surface area is an annular surface area subdivided into segments.

* * * * *